(12) United States Patent
Kim

(10) Patent No.: US 11,576,781 B2
(45) Date of Patent: *Feb. 14, 2023

(54) TRICUSPID REGURGITATION TREATMENT TOOL TO BE INSERTED INTO PULMONARY ARTERY

(71) Applicant: TAU MEDICAL INC., Busan (KR)

(72) Inventor: June Hong Kim, Busan (KR)

(73) Assignee: TAU MEDICAL INC., Busan (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/635,145

(22) PCT Filed: Jul. 27, 2018

(86) PCT No.: PCT/KR2018/008525
§ 371 (c)(1),
(2) Date: Jan. 29, 2020

(87) PCT Pub. No.: WO2019/027183
PCT Pub. Date: Feb. 7, 2019

(65) Prior Publication Data
US 2021/0085451 A1    Mar. 25, 2021

(30) Foreign Application Priority Data
Jul. 31, 2017 (KR) .......................... 10-2017-0096695

(51) Int. Cl.
*A61F 2/24* (2006.01)
(52) U.S. Cl.
CPC ............ *A61F 2/246* (2013.01); *A61F 2/2466* (2013.01); *A61F 2/2476* (2020.05); *A61F 2220/0016* (2013.01)

(58) Field of Classification Search
CPC .................... A61F 2/246; A61F 2/2466; A61F 2220/0008; A61F 2250/0003; A61F 2220/0016
See application file for complete search history.

(56) References Cited

U.S. PATENT DOCUMENTS 7,854,762 B2   12/2010   Speziali et al.
3,486,136 A1    7/2013   Maurer et al.
(Continued)

FOREIGN PATENT DOCUMENTS

CN    102869318 A    1/2013
EP      3662866 A4   5/2021
(Continued)

OTHER PUBLICATIONS

International Preliminary Report on Patentability dated Feb. 4, 2020 of PCT/KR2018/008525.
(Continued)

*Primary Examiner* — Jennifer Dieterle
*Assistant Examiner* — Rebecca Lynee Zimmerman
(74) *Attorney, Agent, or Firm* — Justin Kim

(57) ABSTRACT

A tricuspid regurgitation treatment tool to be inserted into the pulmonary artery is proposed. The tricuspid regurgitation treatment tool to be inserted into the pulmonary artery is used to verify whether the right ventricular dysfunction may occur when treating the tricuspid regurgitation by surgeries or other permanent treatments. A test insertion of the tricuspid regurgitation treatment tool to be inserted into the pulmonary artery is made to pass obliquely through the tricuspid valve of a patient, and after a certain time has elapsed, the tool is removed. The tricuspid regurgitation treatment tool to be inserted into the pulmonary artery includes: a blocking part blocking the tricuspid valve; and an (Continued)

insertion tube provided with a guidewire-guiding lumen formed therein to be movable along the guidewire.

15 Claims, 6 Drawing Sheets

(56) References Cited

U.S. PATENT DOCUMENTS

| | | |
|---|---|---|
| 9,474,605 B2 | 10/2016 | Rowe et al. |
| 11,357,485 B2 | 6/2022 | Kim |
| 2005/0027351 A1 | 2/2005 | Reuter et al. |
| 2006/0064059 A1 | 3/2006 | Gelfand et al. |
| 2007/0198082 A1 | 8/2007 | Kapadia et al. |
| 2007/0239270 A1 | 10/2007 | Mathis et al. |
| 2009/0240326 A1 | 9/2009 | Wilson et al. |
| 2011/0077733 A1 | 3/2011 | Solem |
| 2011/0112632 A1 | 5/2011 | Chau et al. |
| 2011/0257677 A1 | 10/2011 | Carr, Jr. et al. |
| 2012/0172844 A1 | 7/2012 | Mullen |
| 2013/0274645 A1 | 10/2013 | Ferrari |
| 2013/0325110 A1* | 12/2013 | Khalil ............... A61F 2/2427 623/2.11 |
| 2013/0338763 A1* | 12/2013 | Rowe ................. A61F 2/2427 623/2.11 |
| 2015/0366556 A1* | 12/2015 | Khairkhahan ..... A61B 17/0487 606/232 |
| 2016/0213472 A1 | 7/2016 | Kim |
| 2016/0228246 A1 | 8/2016 | Zimmerman |
| 2017/0119489 A1 | 5/2017 | Kim |
| 2021/0085451 A1 | 3/2021 | Kim |

FOREIGN PATENT DOCUMENTS

| | | |
|---|---|---|
| EP | 3662867 A4 | 5/2021 |
| JP | 1992507208 | 12/1992 |
| JP | H11509450 A | 8/1999 |
| JP | 2008536592 A | 9/2008 |
| KR | 20120051936 A | 5/2012 |
| KR | 1020120051936 A | 5/2012 |
| KR | 20130074823 A | 7/2013 |
| KR | 1020130074823 A | 7/2013 |
| KR | 101563172 B1 | 10/2015 |
| KR | 20150144568 A | 12/2015 |
| KR | 1020150144568 A | 12/2015 |
| KR | 20170034088 A | 3/2017 |
| KR | 101730387 B1 | 4/2017 |
| KR | 20170044065 A | 4/2017 |
| KR | 1020170044065 A | 4/2017 |
| KR | 101805679 B1 | 12/2017 |
| NO | 2019027175 A1 | 2/2019 |
| NO | 2019027183 A3 | 3/2019 |

OTHER PUBLICATIONS

International Preliminary Report on Patentability of corresponding international application No. PCT/KR2018/008409 dated Feb. 4, 2020.
International search report (ISR) and written opinion of corresponding international application No. PCT/KR2018/008409 dated Oct. 15, 2018 and Oct. 16, 2018, respectively.
International search report (ISR) of PCT/KR2018/008525 dated Mar. 1, 2019.

* cited by examiner

[FIG. 1]

[FIG. 3]
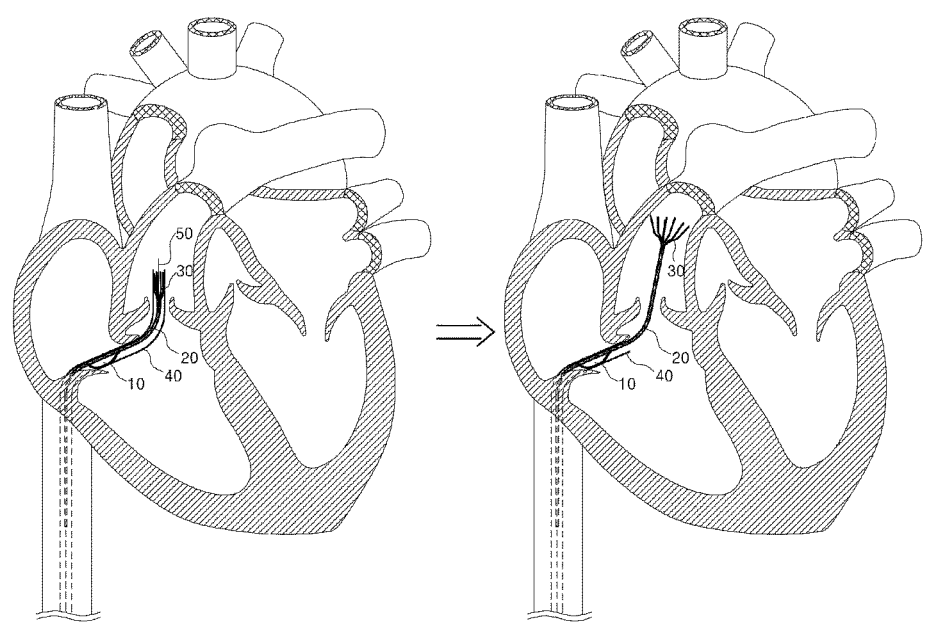

[FIG. 4]
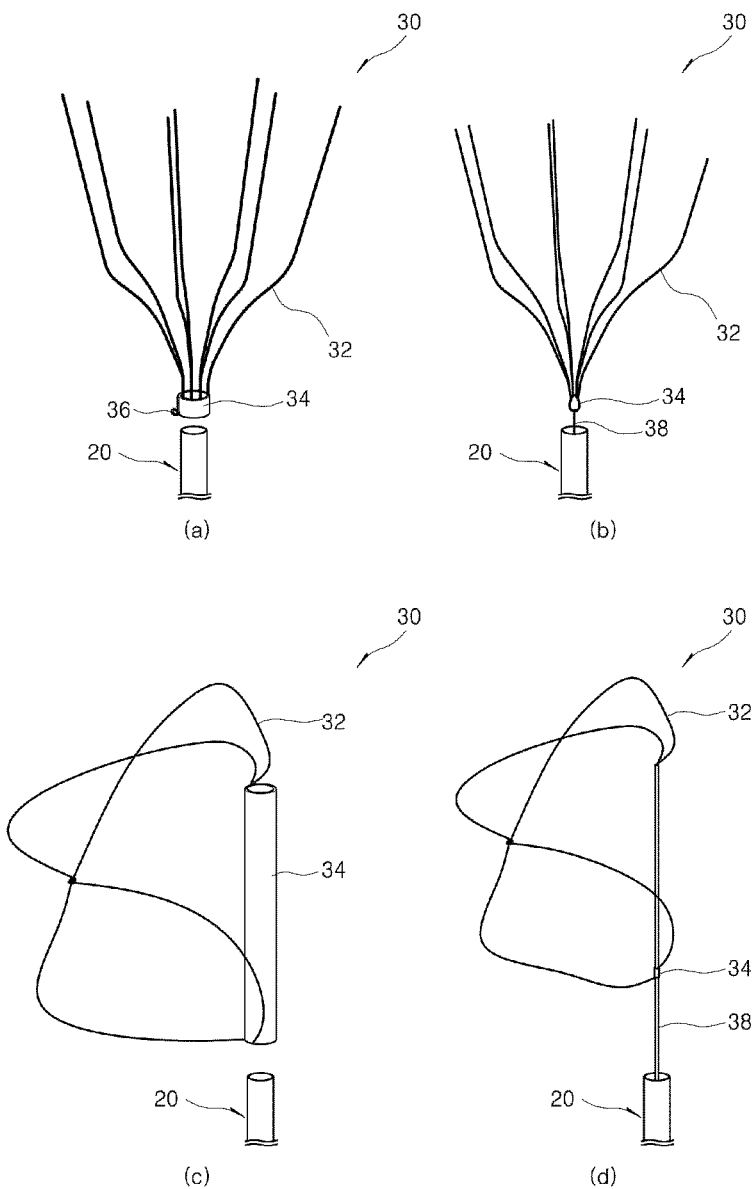

[FIG. 5]
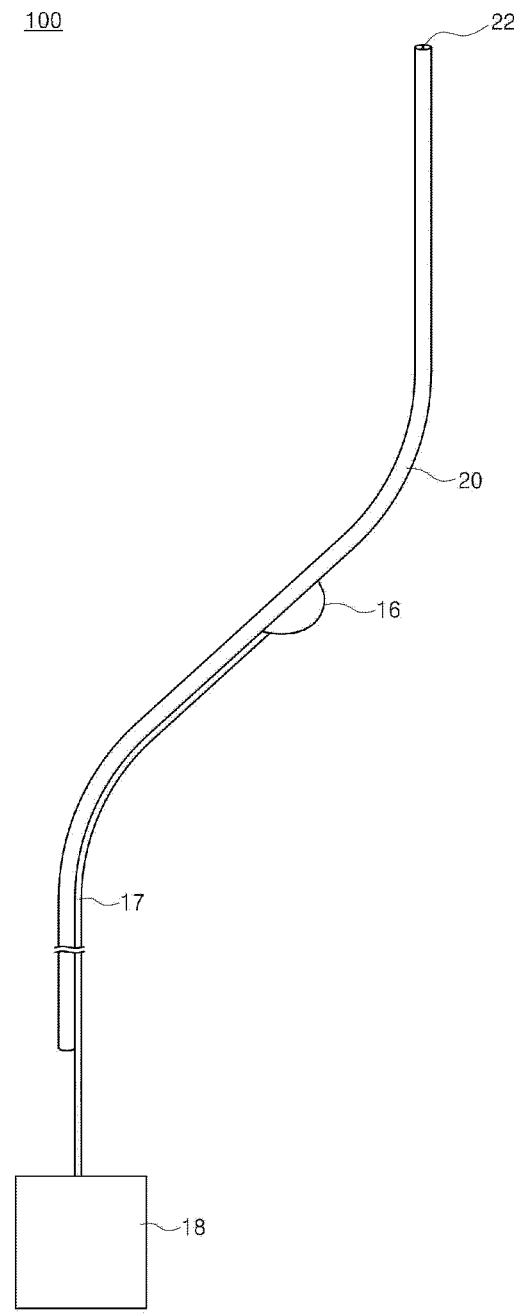

[FIG. 6]
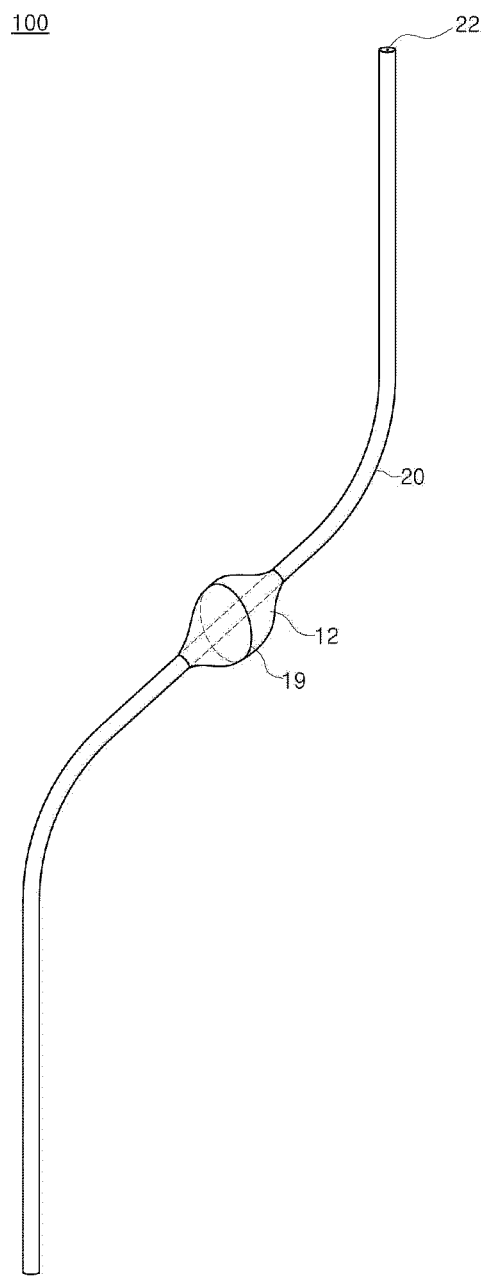

TRICUSPID REGURGITATION TREATMENT TOOL TO BE INSERTED INTO PULMONARY ARTERY

TECHNICAL FIELD

The present invention relates to a tricuspid regurgitation treatment tool to be inserted into the pulmonary artery. More particularly, the present invention relates to a tricuspid regurgitation treatment tool to be inserted into the pulmonary artery, the tool being used to verify whether right ventricular dysfunction may occur when treating tricuspid regurgitation by surgeries or other permanent treatments, wherein a test insertion of the tool is made to pass obliquely through the tricuspid valve of a patient, and after a certain time has elapsed, the tool is removed.

BACKGROUND ART

Tricuspid regurgitation is also called tricuspid valve insufficiency. Tricuspid regurgitation is a lesion of the tricuspid valve, and refers to a symptom in which the tricuspid valve closes incompletely when needed to be closed, thereby resulting in an empty space (i.e., orifice), and thus, some portion of blood, which must flow from the right ventricle into the pulmonary artery during the right ventricular contraction, flows back into the right atrium through the orifice.

Conventional treatment of tricuspid regurgitation includes: a method of surgically remedying the disease by opening the patient's chest and dissecting the heart; and a method of treating tricuspid regurgitation by permanently inserting a tool for treatment of tricuspid regurgitation invented in U.S. Pat. Nos. 8,486,136 B2, 7,854,762 B2, and 9,474,605 B2. However, when treating tricuspid regurgitation by using the above methods or permanent treatments, a sudden increase of blood flow from the right ventricle to the pulmonary artery may cause an overload of the right ventricle, and thus a problem having the right ventricular dysfunction symptom may occur.

DISCLOSURE

Technical Problem

The present invention is to provide a tricuspid regurgitation treatment tool to be inserted into the pulmonary artery, the tool passing obliquely through the tricuspid valve and capable of being easily inserted through the femoral vein, the inferior vena cava, the tricuspid valve, and the pulmonary artery in sequence to solve the above-mentioned problems.

In addition, the present invention is to provide a tricuspid regurgitation treatment tool to be inserted into the pulmonary artery, the tool being capable of verifying whether right ventricle overload occurs by blocking an orifice of the tricuspid valve for only a certain time.

The objectives of the present invention are not limited to the above-mentioned objectives, and other objectives that are not mentioned herein will be clearly understood by those skilled in the art from the following description.

Technical Solution

In order to achieve the above objectives of the present invention, there is provided a tricuspid regurgitation treatment tool to be inserted into the pulmonary artery, the tool including: a blocking part being passed obliquely through the tricuspid valve; and an insertion tube provided with a guidewire-guiding lumen formed therein to be movable from the inferior vena cava to the pulmonary artery along a guidewire.

In addition, the tricuspid regurgitation treatment tool to be inserted into the pulmonary artery may further include: a fixing member for the pulmonary artery capable of temporarily fixing the tricuspid regurgitation treatment tool to be inserted into the pulmonary artery to the pulmonary artery.

The fixing member for the pulmonary artery may include at a lower part thereof: a fixing member body for the pulmonary artery; and a plurality of fixtures for the pulmonary artery radially coupled to the fixing member body for the pulmonary artery.

The fixing member body for the pulmonary artery may be configured in a cylindrical shape having a hole in a central axis thereof and coupled to the insertion tube.

The fixing member body for the pulmonary artery may further include a protruding hook for the pulmonary artery, the protruding hook being coupled to an outer circumferential surface of the fixing member body for the pulmonary artery and capable of being hooked by using a hook inserted from outside.

The fixing member body for the pulmonary artery may be configured in a ring shape, and the fixing member for the pulmonary artery may include a fixing-member-connecting wire having one end thereof coupled to the fixing member body for the pulmonary artery and inserted into the insertion tube.

The fixing member for the pulmonary artery may include: a fixture for the pulmonary artery formed of a wire having a ribbon shape; and a fixing member body for the pulmonary artery coupled to the fixture for the pulmonary artery.

The fixing member body for the pulmonary artery may be configured in a cylindrical shape having a hole in a central axis, and may be coupled to the insertion tube.

The fixing member body for the pulmonary artery may be configured in a ring shape, and the fixing member for the pulmonary artery may include a fixing-member-connecting wire inserted into the insertion tube by passing through a central axis of the fixing member body for the pulmonary artery coupled to the fixture for the pulmonary artery and configured in a ring-shaped wire.

The blocking part may include: a supporting wire having both ends thereof coupled to the insertion tube; and a blocking membrane having one side thereof fixed to the insertion tube and supported by the supporting wire.

The blocking part may be a blocking balloon in a balloon shape capable of expanding or contracting, and may further include: a balloon tube having a first end thereof connected to and communicated with the blocking balloon; and a balloon-adjusting hub connected to a second end of the balloon tube and installed outside a patient's body, the balloon-adjusting hub expanding or contracting the blocking balloon.

The blocking part may include: a ring-shaped wire installed to make the insertion tube to be passed through thereof and having a central axis thereof obliquely formed with respect to the insertion tube; and a blocking membrane connecting the insertion tube and the ring-shaped wire to each other.

In addition, the tricuspid regurgitation treatment tool to be inserted into the pulmonary artery may further include a sheath tube formed with a lumen into which the tricuspid regurgitation treatment tool to be inserted into the pulmonary artery may be inserted to move into a patient's body.

Advantageous Effects

The tricuspid regurgitation treatment tool to be inserted into the pulmonary artery according to the present invention may be easily inserted through the femoral vein, the inferior vena cava, the tricuspid valve, and the pulmonary artery in sequence.

In addition, before the tricuspid regurgitation treatment tool is permanently inserted, it is possible to verify whether the right ventricle is overloaded by temporarily inserting the tricuspid regurgitation treatment tool into a patient's body.

In addition, when an abnormal symptom due to right ventricular overload of the patient is verified, the tool may be easily removed to restore the blood pressure back to normal in the right ventricle.

DESCRIPTION OF DRAWINGS

FIG. 3 is a perspective cross-sectional view showing a process of inserting the tricuspid regurgitation treatment tool to be inserted into the pulmonary artery into a patient's body.

FIG. 4 shows perspective views illustrating each state in which a fixing member for the pulmonary artery is installed at one end of the tricuspid regurgitation treatment tool to be inserted into the pulmonary artery of FIG. 1, wherein FIG. 4a is a perspective view showing a fixing member for the pulmonary artery according to the first exemplary embodiment, FIG. 4b is a perspective view showing a fixing member for the pulmonary artery according to the second exemplary embodiment, FIG. 4c is a perspective view showing a fixing member for the pulmonary artery according to the third exemplary embodiment, and FIG. 4d is a perspective view showing a fixing member for the pulmonary artery according to the fourth exemplary embodiment.

FIG. 5 is a perspective view showing a tricuspid regurgitation treatment tool to be inserted into the pulmonary artery according to another preferred exemplary embodiment of the present invention.

FIG. 6 is a perspective view showing a tricuspid regurgitation treatment tool to be inserted into the pulmonary artery according to yet another preferred exemplary embodiment of the present invention.

DESCRIPTION OF THE REFERENCE NUMERALS IN THE DRAWINGS

Figure 1:
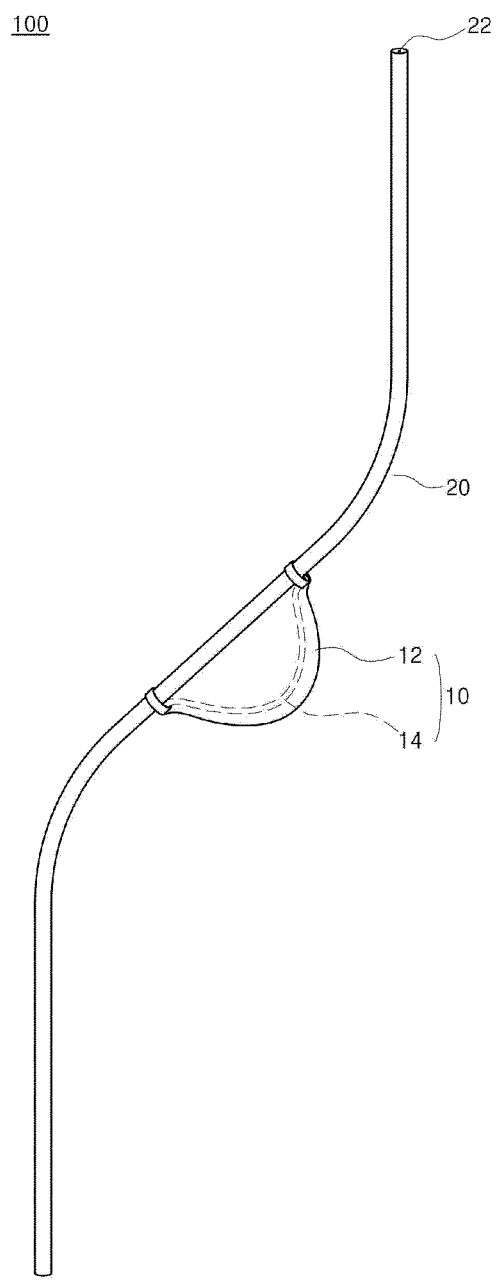
FIG. 1 is a perspective view showing a tricuspid regurgitation treatment tool to be inserted into the pulmonary artery according to a preferred exemplary embodiment of the present invention.

10: blocking part
12: blocking membrane
14: supporting wire
16: blocking balloon
17: balloon tube
18: balloon-adjusting hub
19: ring-shaped wire
20: insertion tube
22: guidewire-guiding lumen
30: fixing member for the pulmonary artery
32: fixture for the pulmonary artery
34: fixing member body for the pulmonary artery
36: protruding hook for the pulmonary artery
38: fixing-member-connecting wire
40: sheath tube
50: guidewire
100: tricuspid regurgitation treatment tool to be inserted into the pulmonary artery
S10: step of moving guidewire
S20: step of moving tricuspid regurgitation treatment tool to be inserted into the pulmonary artery
S30: step of blocking orifice of the tricuspid valve
S40: step of removing tricuspid regurgitation treatment tool to be inserted into the pulmonary artery

BEST MODE

Benefits and features of the present invention, and methods of accomplishing the same may be understood more readily by reference to the following detailed description of exemplary embodiments and the accompanying drawings. However, the present disclosure may be embodied in many different forms, and should not be construed as being limited to the exemplary embodiments set forth herein. Rather, these exemplary embodiments are provided so that this disclosure will be thorough and complete and will fully convey the concept of the invention to those skilled in the art, and the present disclosure will only be defined by the appended claims.

Hereinafter, exemplary embodiments of the present invention will be described in detail with reference to the accompanying drawings. Regardless of the drawings, the same reference numbers refer to the same components, and "and/or" includes each and every combination of one or more of the items mentioned.

The terminology used herein is for the purpose of describing particular embodiments only and is not intended to be limiting of the invention. In this description, the singular also includes the plural unless specifically stated otherwise in the phrase. As used herein, "comprises" and/or "comprising" does not exclude the presence or addition of one or more other components in addition to the mentioned components.

Unless otherwise defined, all terms (including technical and scientific terms) used in the present description may be used in a sense that can be commonly understood by those skilled in the art. In addition, the terms defined in the commonly used dictionaries are not ideally or excessively interpreted unless they are specifically defined clearly.

Hereinafter, the preferred exemplary embodiments of the present invention will be described in detail with reference to the accompanying drawings.

FIG. 1 is a perspective view showing a tricuspid regurgitation treatment tool to be inserted into the pulmonary artery according to a preferred exemplary embodiment of the present invention.

Referring to FIG. 1, the tricuspid regurgitation treatment tool to be inserted into the pulmonary artery 100 includes: a blocking part 10; and an insertion tube 20 provided with a guidewire lumen 22 formed therein.

The blocking part 10 includes: a supporting wire 14 having both ends fixed to the insertion tube 20; and a blocking membrane 12 connecting the insertion tube 20 and the supporting wire 14 to each other. It is apparent that two opposite sides or one side of the supporting wire 14 may not be fixed to the insertion tube 20.

The blocking membrane 12 has softness but not easily torn, is made of a material suitable for the human body, and may be made of a material such as medical polyurethane, polyolefin, silicone, e-PTFE, and PTFE.

The supporting wire 14 is to hold the shape of the blocking membrane 12, and may be made of a synthetic resin wire such as nylon or a metal wire (i.e., stainless steel, nylon coating on metal, etc.), and the like. It is apparent that the supporting wire 14 may be a single wire, and may also be a form of wire made by twisting a plurality of thin wires. The blocking membrane 12 may be provided in two layers and configured to be a form where the supporting wire 14 is inserted into the blocking membrane 12.

As shown in FIG. 1, the blocking membrane 12 may have a circular shape as well as a semi-circular shape, and a plurality of insertion tubes 20 may also be installed therein to adjust the position or to fix the shape of the blocking membrane 12 having the circular shape.

The insertion tube 20 provided with a guidewire-guiding lumen 22 formed therein may be made of a material such as rubber and soft plastic, and is made of a material with high softness and having excellent flexibility and resilience to be movable according to the heartbeat.

Figure 2:
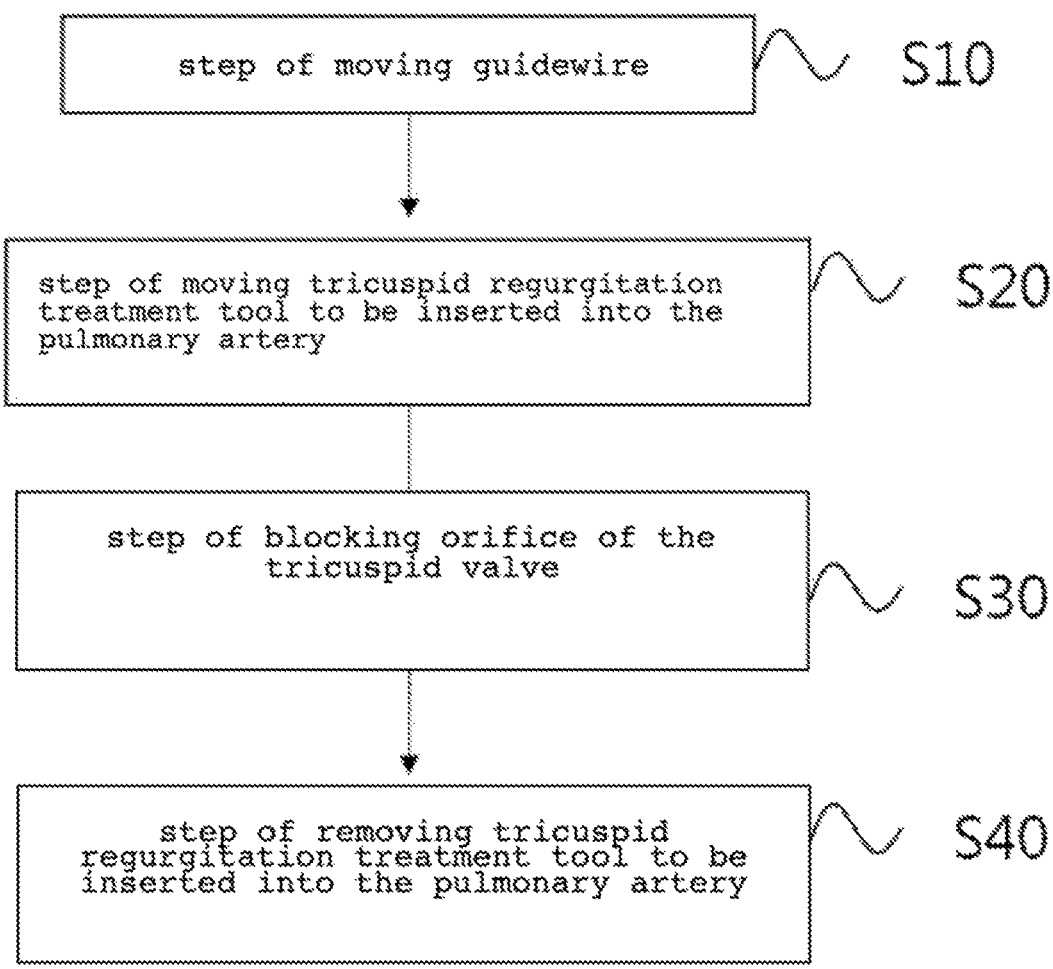
FIG. 2 is a flowchart showing steps of treating tricuspid regurgitation by pulmonary artery insertion using the tricuspid regurgitation treatment tool to be inserted into the pulmonary artery of the present invention.

FIG. 2 is a flowchart showing steps of treating tricuspid regurgitation for pulmonary artery insertion using the tricuspid regurgitation treatment tool to be inserted into the pulmonary artery of the present invention, and FIG. 3 is a perspective cross-sectional view showing a process of inserting the tricuspid regurgitation treatment tool to be inserted into the pulmonary artery into a patient's body.

Referring to FIGS. 2 and 3, steps of treating tricuspid regurgitation for pulmonary artery insertion include: a step of moving guidewire S10; a step of moving tricuspid regurgitation treatment tool to be inserted into the pulmonary artery S20; a step of blocking orifice of the tricuspid valve S30; and a step of removing the tricuspid regurgitation treatment tool to be inserted into the pulmonary artery S40.

The step of moving guidewire S10 is a step to move the guidewire 50 through the femoral vein, the inferior vena cava, the tricuspid valve, and the pulmonary artery in sequence so as to facilitate the movement of the tricuspid regurgitation treatment tool to be inserted into the pulmonary artery 100 of the present invention. The movement of the wires and catheters in the patient's body may be observed through X-rays. In order to safely move the guidewire 50 into the patient's body, a guidewire-guiding tube (not shown) having a lumen formed therein is required. At the upper end thereof, the guidewire-guiding tube (not shown) has a balloon or a pigtail-shaped locking means to pass through the safe zone of the tricuspid valve. Around the tricuspid valve, there are leaflets of the tricuspid valve, subvalvular structures such as the chordae tendineae and the papillary muscles of the tricuspid valve, and the modulator band. This space is called the unsafe zone. In addition to the unsafe zone, the safe zone refers to a safe area where the human body is not damaged even when wires or catheters pass through the area. The locking means prevents the guidewire-guiding tube from moving forward by being caught in the subvalvular structures and the moderator band when moving toward the unsafe zone, thereby allowing moving to only the safe zone. Accordingly, after the guidewire-guiding tube (not shown) is inserted through the femoral vein, the inferior vena cava, the safe zone of the tricuspid valve, and the pulmonary artery in sequence, the guidewire 50 is inserted into the guidewire-guiding tube (not shown) to move safely inside the patient's body. When the guidewire 50 reaches the pulmonary artery, the movement is stopped and the guidewire-guiding tube (not shown) is removed out of the patient's body. At this time, the tricuspid regurgitation treatment tool to be inserted into the pulmonary artery 100 is inserted into the sheath tube 40 having a lumen formed therein, and is prepared to move into the patient's body.

The step of moving tricuspid regurgitation treatment tool to be inserted into the pulmonary artery S20 is a step of inserting the guidewire 50 into the guidewire-guiding lumen 22 formed in the insertion tube 20 so as to move the tricuspid regurgitation treatment tool to be inserted into the pulmonary artery 100 into the patient's body. Along the path (i.e., the femoral vein, the inferior vena cava, the tricuspid valve, and the pulmonary artery in sequence) where the guidewire 50 is moved in the patient's body, the tricuspid regurgitation treatment tool to be inserted into the pulmonary artery 100 inserted into the sheath tube 40 is moved.

The step of blocking orifice of the tricuspid valve S30 is a step of inserting the tricuspid regurgitation treatment tool to be inserted into the pulmonary artery 100 into the patient's body to block the orifice of the tricuspid valve by the blocking part 10. When the blocking part 10 passes obliquely through the tricuspid valve, the guidewire 50 and the sheath tube 40 are removed out of the patient's body to block the orifice of the tricuspid valve for a certain time.

The step of removing the tricuspid regurgitation treatment tool to be inserted into the pulmonary artery S40 is a step of removing the tricuspid regurgitation treatment tool to be inserted into the pulmonary artery 100 out of the patient's body after verifying whether the patient shows abnormal symptoms such as right ventricular dysfunction and determining whether a permanent treatment is applicable. After blocking the orifice of the tricuspid valve, in the case when the symptoms do not appear even after a certain time, the sheath tube 40 is inserted into the patient's body again. The tricuspid regurgitation treatment tool to be inserted into the pulmonary artery 100 is inserted into the sheath tube 40, and the tricuspid regurgitation treatment tool to be inserted into the pulmonary artery 100 inserted into the sheath tube 40 is removed out of the patient's body. In the case when any abnormal symptom appears, the tricuspid regurgitation treatment tool to be inserted into the pulmonary artery 100 is immediately removed out of the patient's body.

According to the above steps, by temporarily blocking the orifice of the tricuspid valve before the tricuspid regurgitation is permanently treated for the patient with tricuspid regurgitation, whether the tricuspid regurgitation may be treated or not may be verified.

FIG. 4 shows perspective views illustrating each state in which a fixing member for the pulmonary artery is installed at one end of the tricuspid regurgitation treatment tool to be inserted into the pulmonary artery of FIG. 1, wherein FIG. 4a is a perspective view showing a fixing member for the pulmonary artery according to the first exemplary embodiment, FIG. 4b is a perspective view showing a fixing member for the pulmonary artery according to the second exemplary embodiment, FIG. 4c is a perspective view showing a fixing member for the pulmonary artery according to the third exemplary embodiment, and FIG. 4d is a perspective view showing a fixing member for the pulmonary artery according to the fourth exemplary embodiment.

Referring to FIG. 4, at the upper end thereof, the tricuspid regurgitation treatment tool to be inserted into the pulmonary artery 100 of the present invention may further include a fixing member for the pulmonary artery 30.

First, referring to FIG. 4a, the fixing member for the pulmonary artery 30 according to the first exemplary embodiment includes at the lower part thereof: a fixing member body for the pulmonary artery 34; and a plurality of fixtures for the pulmonary artery 32 radially coupled to the fixing member body for the pulmonary artery 34. The fixing member body for the pulmonary artery 34 is configured in a cylindrical shape having a hole in a central axis thereof, has the inner circumferential surface thereof closely coupled to the outer circumferential surface of the insertion tube 20, and is fitted to the insertion tube 20. In addition, the fixing member body for the pulmonary artery 34 may further include a protruding hook for the pulmonary artery 36 having a ring shape formed on the outer circumferential surface thereof.

Referring to FIG. 4b, the fixing member for the pulmonary artery 30 according to the second exemplary embodiment includes at the lower part thereof: a fixing member body for the pulmonary artery 34 having a ring shape; a plurality of fixtures for the pulmonary artery 32 radially coupled to the upper end of the fixing member body for the pulmonary artery 34; and a fixing-member-connecting wire 38 having one end thereof coupled to the fixing member body for the pulmonary artery 34 and inserted into the insertion tube 20.

The fixture for the pulmonary artery 32 according to the first exemplary embodiment and the second exemplary embodiment may be made of an elastic body, a shape memory alloy, or a self-expandable stent. When inserted into the sheath tube 40 to move into the patient's body, the fixture for the pulmonary artery 32 is inserted in a folded state. When the sheath tube is removed, the fixture for the pulmonary artery 32 is returned to its original state and unfolded in a radial shape, and fixed to the pulmonary artery.

Referring to FIG. 4c, the fixing member for the pulmonary artery 30 according to the third exemplary embodiment includes: the fixture for the pulmonary artery 32 formed of a wire having a ribbon shape with a convex central part; the fixing member body for the pulmonary artery 34 coupled to the lower end of the fixture for the pulmonary artery 32; and the protruding hook for the pulmonary artery 36 formed on the outer circumferential surface of the fixing member body for the pulmonary artery 34. The fixing member body for the pulmonary artery 34 is configured in a cylindrical shape having a hole in a central axis thereof, is provided with the inner circumferential surface thereof that is tightly coupled to the outer circumferential surface of the insertion tube 20, and is fitted to the insertion tube 20.

The fixture for the pulmonary artery 32, formed of a wire having a ribbon shape with a convex central part, may be made of a shape memory alloy, an elastic body, or a self-expanding stent. When inserted into the sheath tube 40 in order to be inserted into the patient's body, the fixture for the pulmonary artery 32 is inserted while the convex central part is pressed. Also, when the sheath tube 40 is removed, the fixture for the pulmonary artery 32 is returned to its ribbon shape with the convex central part and fixed to the pulmonary artery.

Referring to FIG. 4d, the fixing member for the pulmonary artery 30 according to the fourth exemplary embodiment includes: a fixture for the pulmonary artery 32 formed of a wire having a ribbon shape; a fixing member body for the pulmonary artery 34 formed in a ring shape and coupled to the lower end of the fixture for the pulmonary artery 32; and a fixing-member-connecting wire 38 coupled to one end of the fixture for the pulmonary artery 32 and passing through the central axis of the fixing member body for the pulmonary artery 34, and inserted into the insertion tube 20.

The fixture for the pulmonary artery 32 formed in the ribbon shape according to the fourth exemplary embodiment is inserted into the sheath tube 40 and moved into the patient's body in order to be inserted into the patient's body. When the sheath tube 40 is removed, the fixture for the pulmonary artery 32 pushes the fixture for the pulmonary artery 32 or the fixing member body for the pulmonary artery 34 forward to make the fixture for the pulmonary artery 32 have the ribbon shape with the convex central part thereof and be fixed to the pulmonary artery.

Different forms other than the fixing member for the pulmonary artery 30 of the above-described form are also applicable. In addition, the fixing member for the pulmonary artery 30 may be coupled to the lower end of the insertion tube 20 and fixed to the inferior vena cava.

In the case of removing the fixing member for the pulmonary artery 30, there is a method in which the sheath tube is reinserted into the patient's body and the tricuspid regurgitation treatment tool to be inserted into the pulmonary artery 100 is inserted into the sheath tube 40 for removal, or alternatively, there is a method in which the fixing member for the pulmonary artery 30 is hooked on the protruding hook for the pulmonary artery 36 and pulled out of the patient's body after additionally inserting a wire (not shown) having a hook shape at the upper end thereof into the patient's body.

It is apparent that the fixing member for the pulmonary artery 30 may not be installed in the tricuspid regurgitation treatment tool to be inserted into the pulmonary artery 100.

FIG. 5 is a perspective view showing a tricuspid regurgitation treatment tool to be inserted into the pulmonary artery according to another preferred exemplary embodiment of the present invention.

Referring to FIG. 5, the tricuspid regurgitation treatment tool to be inserted into the pulmonary artery 100 according to another preferred exemplary embodiment of the present invention includes: an insertion tube 20 provided with a lumen 22; and a blocking part 10. The insertion tube 20 is the same as described above in FIG. 1. The blocking part 10 includes: a blocking balloon 16 coupled to one side of the insertion tube 20; the balloon tube 17 having one end thereof connected to and communicated with the blocking balloon 16; and the balloon-adjusting hub 18 coupled to the other end of the balloon tube 17 and adjusting the expansion and contraction of the blocking balloon 16. The balloon-adjusting hub 18 is installed outside the patient's body, and the blocking balloon 16 may be expanded or contracted by air, oxygen, foam, and the like supplied from the balloon-adjusting hub 18.

The tricuspid regurgitation treatment tool to be inserted into the pulmonary artery 100 may further include a fixing member for the pulmonary artery 30, and the fixing member for the pulmonary artery 30 is the same as described above with reference to FIG. 4.

When moved into the patient's body, the fixing member for the pulmonary artery 30 of the second and the fourth exemplary embodiments may not be inserted into the sheath tube 40. After the fixing-member-connecting wire 38 is pulled downward and inserted into the insertion tube 20 to move the fixing member for the pulmonary artery 30, when stopped moving, by pushing the fixing-member-connecting wire 38 upward, the fixing member for the pulmonary artery 30 may be taken out of the insertion tube 20 and fixed to the pulmonary artery.

FIG. 6 is a perspective view showing a tricuspid regurgitation treatment tool to be inserted into the pulmonary artery according to yet another preferred exemplary embodiment of the present invention.

Referring to FIG. 6, the tricuspid regurgitation treatment tool to be inserted into the pulmonary artery 100 according to yet another preferred exemplary embodiment of the present invention includes: an insertion tube 20 provided with a lumen 22 formed therein; and a blocking part 10. The insertion tube 20 is the same as described above in FIG. 1. The blocking part 10 includes: a ring-shaped wire 19 installed to make the insertion tube 20 to be passed through thereof and having a central axis thereof obliquely formed with respect to the insertion tube 20; and a blocking membrane 12 connecting the ring-shaped wire 19 and the insertion tube 20 to each other.

The tricuspid regurgitation treatment tool to be inserted into the pulmonary artery 100 may further include a fixing member for the pulmonary artery 30, and the fixing member for the pulmonary artery 30 is the same as described above with reference to FIG. 4.

Since the ring-shaped wire 19 is installed obliquely with respect to the insertion tube 20 at a certain angle, the ring-shaped wire 19 is positioned in parallel to the tricuspid valve. Thus, the orifice of the tricuspid valve may be effectively blocked.

Although the exemplary embodiments of the present invention have been described above with reference to the accompanying drawings, it will be understood that those skilled in the art to which the present invention pertains may implement the present invention in other specific forms without departing from the technical spirit or essential features thereof. Therefore, the exemplary embodiments described above are to be understood in all respects as illustrative and not restrictive.

The invention claimed is:

1. A tricuspid regurgitation treatment tool to be inserted into the pulmonary artery, the tool comprising:
a sheath tube;
an insertion tube inside the sheath tube;
a blocking part on the insertion tube with the blocking part inside the sheath tube and moveable in and out of therein, wherein the blocking part has a compact configuration when inside the sheath tube and an expanded configuration when outside the sheath tube;
a pulmonary artery fixing member inside the sheath tube and moveable in and out of therein, wherein the pulmonary artery fixing member has a compact configuration when inside the sheath tube and an expanded configuration when outside the sheath tube;
wherein the insertion tube has a distal bend with a first predetermined curvature at a location distal to the blocking part, wherein the first predetermined curvature is oriented in a first direction;
wherein the insertion tube further has a proximal bend with a second predetermined curvature at a location proximal to the blocking part, wherein the second predetermined curvature is oriented in a second direction.

2. The tool of claim 1, wherein the pulmonary artery fixing member comprises at a lower part thereof:
a fixing member body; and
a plurality of fixtures radially coupled to the fixing member body.

3. The tool of claim 2, wherein the fixing member body is configured in a cylindrical shape having a hole in a central axis thereof and coupled to the insertion tube.

4. The tool of claim 3, wherein the fixing member body further comprises a protruding hook.

5. The tool of claim 2, wherein the fixing member body is configured in a ring shape, and the pulmonary artery fixing member comprises a connecting wire having one end thereof coupled to the fixing member body and inserted into the insertion tube.

6. The tool of claim 1, wherein the pulmonary artery fixing member comprises:
a fixture formed of a wire having a ribbon shape; and
a fixing member body coupled to the fixture.

7. The tool of claim 6, wherein the fixing member body is configured in a cylindrical shape having a hole in a central axis, and is coupled to the insertion tube.

8. The tool of claim 6, further comprising a connecting wire traveling inside the insertion tube, wherein the pulmonary artery fixing member is attached to a distal end of the connecting wire.

9. The tool of claim 1, wherein the blocking part comprises:
a supporting wire having both ends thereof coupled to the insertion tube; and
a blocking membrane having one side thereof fixed to the insertion tube and supported by the supporting wire.

10. The tool of claim 1, wherein the blocking part is a blocking balloon in a balloon shape capable of expanding or contracting, and the tool further comprises:
a balloon tube having a first end thereof connected to and communicated with the blocking balloon; and
a balloon-adjusting hub connected to a second end of the balloon tube, the balloon-adjusting hub being operable for expanding or contracting the blocking balloon.

11. The tool of claim 1, wherein the blocking part comprises:
a ring-shaped wire; and
a blocking membrane held by the ring-shaped wire.

12. The tool of claim 1, wherein the second direction is different from the first direction.

13. The tool of claim 12, wherein the second direction is opposite from the first direction.

14. The tool of claim 13, the proximal bend is mirror symmetrical to the distal bend.

15. The tool of claim 1 wherein the insertion tube consists of only a single bend proximal to the blocking part, wherein said single bend is the proximal bend.

* * * * *